United States Patent
Lippitt et al.

(10) Patent No.: US 7,210,210 B2
(45) Date of Patent: May 1, 2007

(54) METHOD OF MAKING A MEDICAL GRASPER

(75) Inventors: Robert G. Lippitt, Smithfield, NC (US); Raymond F. Lippitt, Bethesda, MD (US); Andrew R. Leopold, Lake Zurich, IL (US)

(73) Assignee: Lippitt Extractor Company, LLC, Smithfield, NC (US)

( * ) Notice: Subject to any disclaimer, the term of this patent is extended or adjusted under 35 U.S.C. 154(b) by 384 days.

(21) Appl. No.: 10/445,086

(22) Filed: May 27, 2003

(65) Prior Publication Data

US 2003/0225419 A1 Dec. 4, 2003

Related U.S. Application Data

(60) Provisional application No. 60/386,190, filed on May 28, 2002.

(51) Int. Cl.
*A61B 17/22* (2006.01)
*B23P 11/02* (2006.01)

(52) U.S. Cl. .......................... 29/447; 29/516; 606/113; 606/127

(58) Field of Classification Search ............... 29/447, 29/516; 606/110, 113, 127
See application file for complete search history.

(56) References Cited

U.S. PATENT DOCUMENTS 5,906,622 A * 5/1999 Lippitt et al. ............... 606/127
5,924,175 A * 7/1999 Lippitt et al. ................. 24/537
6,077,274 A * 6/2000 Ouchi et al. ................ 606/113
6,368,327 B2 * 4/2002 Lippitt et al. ............... 606/110

* cited by examiner

*Primary Examiner*—Jermie E. Cozart
(74) *Attorney, Agent, or Firm*—Brinks Hofer Gilson & Lione (57) ABSTRACT

A method of forming an annularly expanding and retracting gripping and releasing mechanism providing a series of flexible tubes, comprising providing (1) a series of flexible tubes, (2) a corresponding series of wires, each of which includes a movable wire section and relatively short fixed wire section integrally connected with one end of the movable wire section by a kink configured so that the wire sections extend in longitudinally coextensive relation therefrom; (3) a series of tubular elements of thermoplastic material; and (4) a series of heat shrinkable sleeves assembling a distal end portion of each flexible tube with a fixed wire section, a tubular element and a heat shrinkable sleeve so that the fixed wire section extends along the exterior periphery of the flexible tube with the kink disposed outwardly of the distal end thereof. The tubular element is disposed in surrounding relation to the fixed wire section and the flexible tube and the heat shrinkable sleeve is disposed in surrounding relation to the tubular element. The method further comprises applying heat to the exterior of each heat shrinkable sleeve at a temperature sufficient to contract the sleeve and soften the thermoplastic material of the tubular element surrounded thereby so that the contraction of the sleeve molds the softened thermoplastic material into adhered contact with the exterior surfaces of the surrounded fixed wire section and flexible tube.

15 Claims, 12 Drawing Sheets

METHOD OF MAKING A MEDICAL GRASPER

CROSS REFERENCE TO RELATED APPLICATIONS AND PATENTS

The present application claims priority from provisional application 60/386,190, filed May 28, 2002, the disclosure of which is hereby incorporated by reference into the present specification. The subject matter of the application relates to improvements in medical extractors or graspers of the type disclosed in U.S. Pat. No. 5,906,622, the disclosure of which is hereby incorporated by reference into the present specification.

BACKGROUND OF THE INVENTION

The extractor disclosed in the '622 patent comprises an elongated cannula assembly having an annularly expanding and retracting gripping and releasing mechanism at the distal end thereof and a moving assembly at the proximal end thereof. The gripping and releasing mechanism includes an annular series of longitudinally fixed flexure elements and a corresponding series of longitudinally movable flexure elements. The moving assembly is operable to effect a relative movement between the flexure elements to move them between a retracted condition and an expanded condition defined by an annular series of transversely outwardly flexed fixed elements interconnected by an annular series of arcuately flexed portions of said flexure elements.

While the disclosed configurations of the '622 patent when made with relatively large dimensions are satisfactory, difficulties occur in attempting to miniaturize the disclosed constructions into a three French size such as required by many popular scopes. These size restrictions create an especially troublesome problem in providing a cost effective construction and method for making the gripping and releasing mechanism embodied in a medical device suitable for both extracting stones directly from the kidneys as well as extracting stones from the ureter. This is because of the chamber configuration of the kidneys, which make the usual closed pointed end of a urethral basket, which operates in the elongated tubular configuration of the ureter, inappropriate. Moreover, it is necessary to negotiate a severe turn to get to the kidney chambers. The heart of the problem lies in the construction and method used to accomplish the connection between each movable flexure element and the distal end of a corresponding fixed flexure element. Several different arrangements are disclosed in the above cited patent, but none have appeared on the commercial market. There exists a need to provide a commercially acceptable cost effective construction and method for forming a gripping and releasing mechanism of the type described which solves the identified problem.

BRIEF SUMMARY OF THE INVENTION

An object of the invention is to fulfill the need expressed above. In accordance with the principles of the present invention, this objective is achieved by providing a method of forming an annularly expanding and retracting gripping and releasing mechanism suitable for use as a stone grasper. The gripping and releasing mechanism comprises an annular array of fixed flexure elements fixed together at proximal ends thereof and corresponding movable flexure elements fixed with respect to distal ends of respective fixed flexure elements and movable within respective adjacent fixed flexure elements. This method enables movement of the movable flexure elements outwardly of the fixed flexure elements which causes the fixed flexure elements to flex transversely outwardly and create an expanded condition. This expanded condition is defined by an annular series of transversely outwardly flexed fixed flexure elements interconnected by an annular series of arcuately flexed portions of the movable flexure elements. The grasper also enables movement of the movable flexible elements when in an expanded condition in a direction inwardly of the fixed flexure elements which causes the expanded condition to progressively retract.

The method comprises a series of steps including the step of providing: (1) a series of flexible tubular structures, (2) a corresponding series of wires, each of which includes a movable wire section and relatively short fixed wire section integrally connected with one end of the movable wire section by a kink configured so that the wire sections extend in longitudinally coextensive relation therefrom; (3) a series of tubular elements of thermoplastic material; and (4) a series of heat shrinkable sleeves. The series of steps also includes the step of assembling a movable wire section within each flexible tubular structure and a distal end portion of each flexible tubular structure with a fixed wire section, a tubular element and a heat shrinkable sleeve so that the (1) fixed wire section extends along the exterior periphery of the flexible tubular structure with the kink disposed outwardly of the distal end thereof, (2) the tubular element is disposed in surrounding relation to the fixed wire section and the flexible tubular structure and (3) the heat shrinkable sleeve is disposed in surrounding relation to the tubular element. The method also comprises the step of applying heat to the exterior of each heat shrinkable sleeve at a temperature sufficient to contract the sleeve and soften the thermoplastic material of the tubular element surrounded thereby so that the contraction of the sleeve molds the softened thermoplastic material into adhered contact with the exterior surfaces of the surrounded fixed wire section and flexible tubular structure. One more step of the method comprises fixedly securing the flexible tubular structures together adjacent the proximal ends of the heat shrinkable sleeves disposed in surrounding relation to the tubular elements.

The objective is also obtained by providing a medical grasper which comprises an annular array of flexible thin walled wire receiving tubular structures and a wire associated with each wire receiving tubular structure. Each wire includes a long movable section movably extending within one of the wire receiving tubular structures and a short fixed section integrally connected with one end of the movable section by a kink. In the medical grasper the main extent of the wire receiving tubular structures, except for short distal end portions thereof are contained together in coextensive relation to form a fixed part of an elongated cannula assembly. The short distal end portion of each wire receiving tubular structure is capable of independent flexure and has a fixed wire section extending along an exterior periphery thereof and a molded annular body of thermoplastic material surrounding the exterior periphery thereof in adhered relation thereto and to the fixed wire section extending therealong to retain the fixed wire section in fixed relation thereon.

Distal end portions of the wire receiving tubular structures, the fixed wire sections fixed thereto and the molded bodies of thermoplastic material surrounding the same constitute an annular array of fixed flexure elements fixed together at the distal end of the cannula assembly and extending therefrom. Distal end portions of the movable wire sections define the movable flexure elements movable within the fixed flexure elements.

A moving assembly on the proximal end of the cannula assembly is constructed and arranged so that (1) a movement of the moving assembly in one direction will effect a movement of the movable flexure elements outwardly of the fixed flexure elements to extend in an arcuately flexed condition outwardly of the fixed flexure elements to cause the latter to flex transversely outwardly and create an expanded condition defined by an annular series of transversely outwardly flexed fixed flexure elements interconnected by an annular series of arcuately flexed portions of the movable flexure elements; and (2) a manual movement in an opposite direction will effect a movement of the movable flexure elements when in an expanded condition in a direction inwardly of the fixed flexure elements to cause the expanded condition to progressively retract during which the annular series of transversely outwardly flexed fixed flexure elements are progressively less flexed transversely outwardly and the annular series of arcuately flexed portions of the movable flexure elements have a progressively less arcuate extent.

DESCRIPTION OF THE PREFERRED EMBODIMENT

Referring now more particularly to the drawings, there is shown therein a medical grasper, generally indicated at 10, embodying the principles of the present invention. The medical grasper 10 as shown includes, in general, an elongated cannula assembly, generally indicated at 12, having an expandable and retractable gripping and releasing mechanism, generally indicated at 14, on the distal end thereof and a moving handpiece assembly, generally indicated at 16, on the proximal end thereof. The moving assembly 16 is manually operable to expand and retract the gripping and releasing mechanism 14. As shown, the cannula assembly 12 of the medical extractor 10 is capable of being inserted through the central passage of a conventional scope deployed within a patient with the gripping and releasing mechanism 14 extending within the patient outwardly of the distal end of the scope and the moving assembly 16 disposed inwardly of the proximate end of the scope exteriorly of the patient. The construction of the grasper 10, as shown, can be made to pass through the central passage of a scope which measures three French.

The cannula assembly 12 and the gripping and releasing mechanism 14 constitute a subassembly of the grasper 10 which is preferably made in accordance with a method embodying the principles of the present invention. The starting materials used in practicing the method of the present invention to make the gripping and releasing mechanism 14 include (1) a series (three) of flexible wire receiving tubular structures 18 and (2) a corresponding number of elongated wires, generally indicated at 20. Each wire 20 includes a relatively long movable wire section 22 and a relatively short fixed wire section 24 integrally connected with one end of the movable wire section 22 by a kink 26. The starting materials also include (3) a corresponding number of tubular elements 28 of thermoplastic material; and (4) A corresponding number of heat shrinkable sleeves 30.

Figure 1:
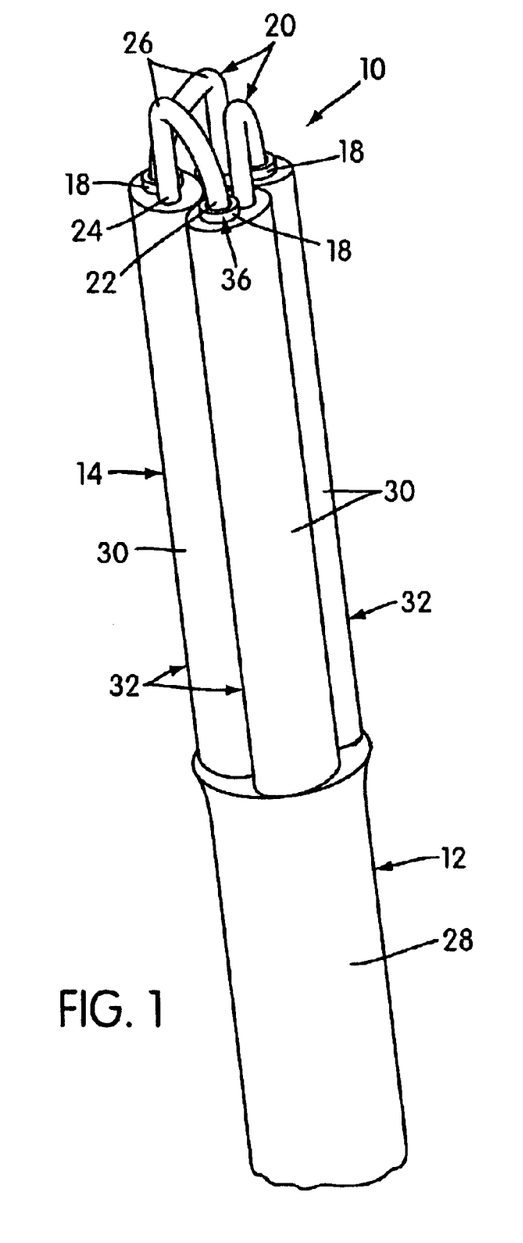
FIG. 1 is a fragmentary perspective view looking down on the distal end of the gripping and releasing mechanism and adjacent portion of the cannula assembly of a medical grasper embodying the principles of the present invention, the parts being shown in a closed position.
Figure 3:
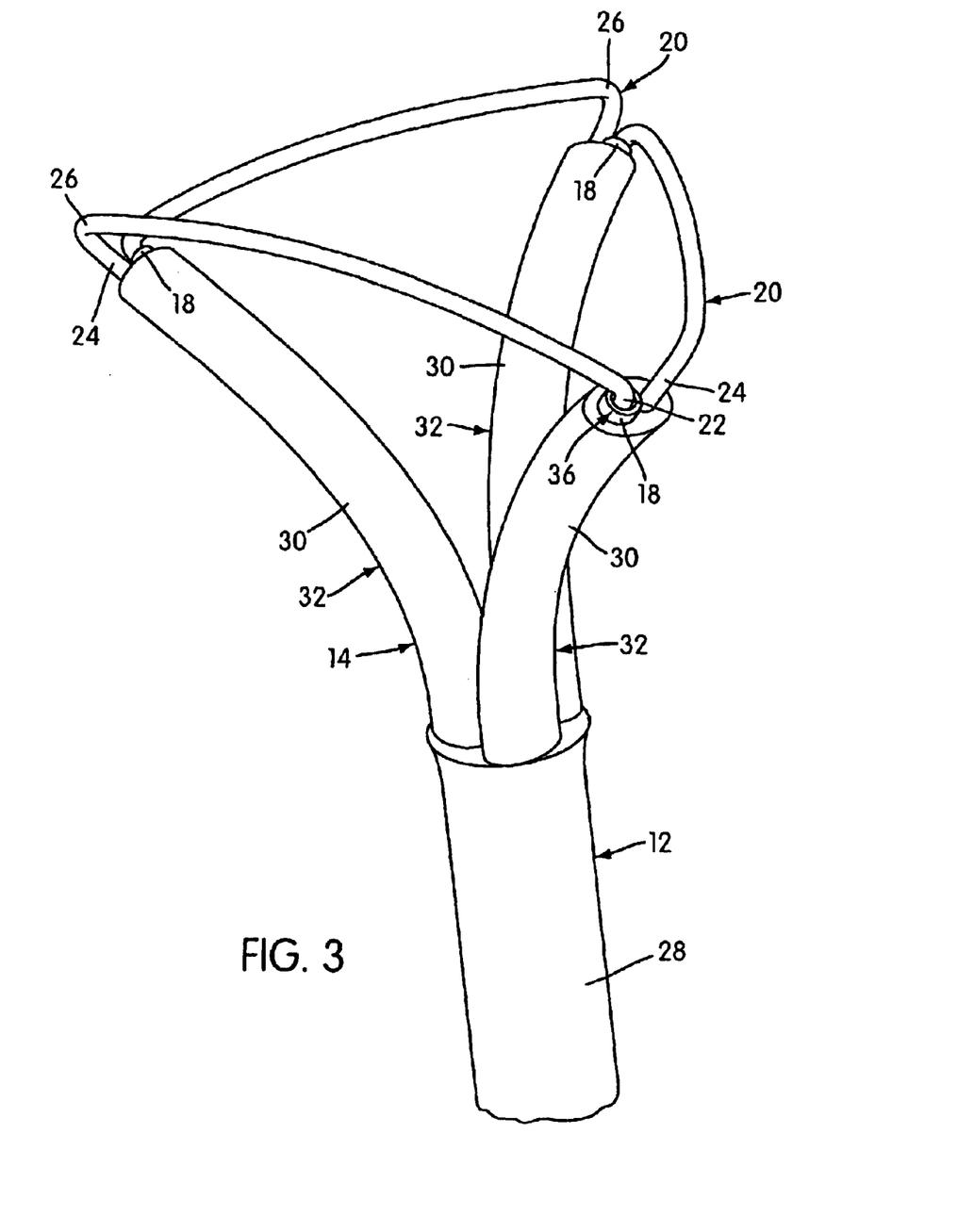
FIG. 3 is a view similar to FIG. 1 showing the parts in an open position.
Figure 4:
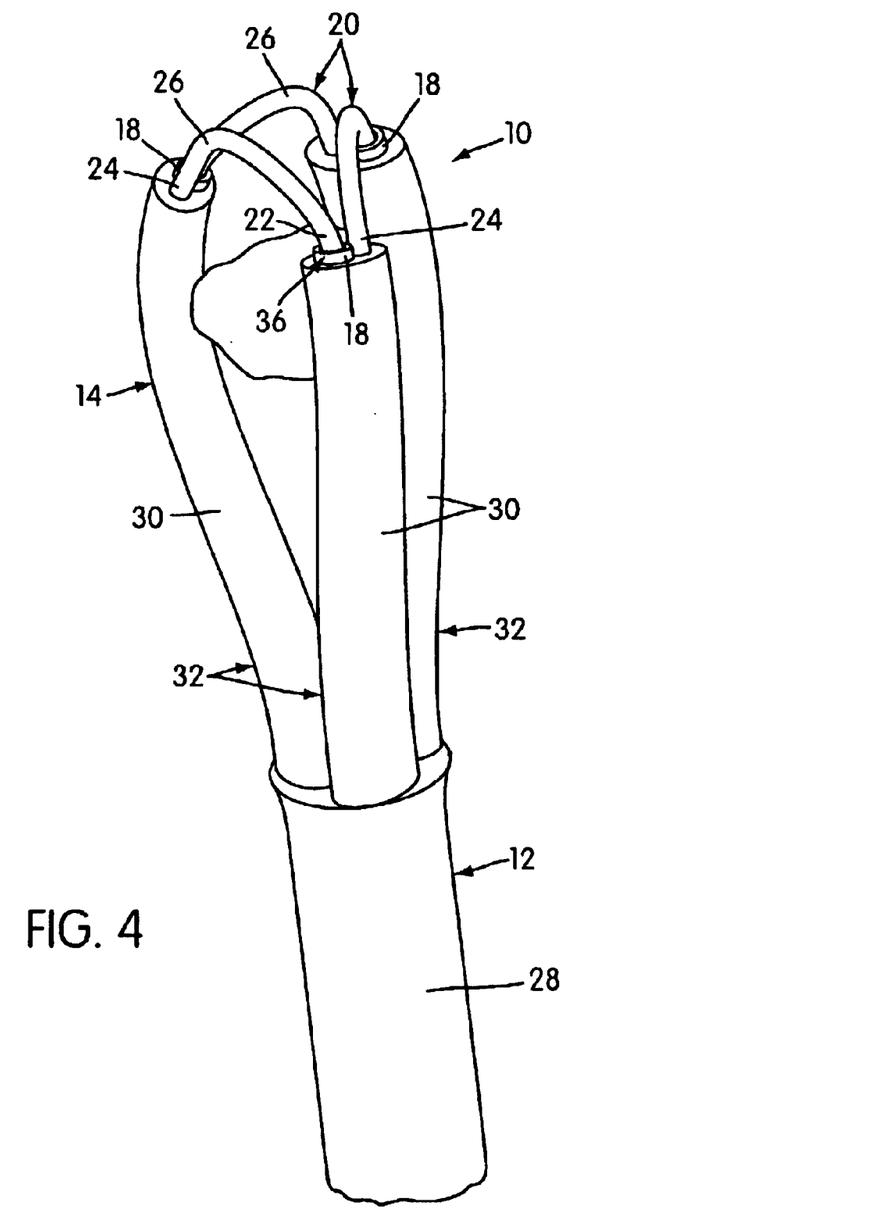
FIG. 4 is a view similar to FIGS. 1 and 3 showing the parts in a stone gripping position.

The tubular structures 18 shown in FIGS. 1, 3 and 4 are tubes made of a flexible, thin walled plastic material capable of stably withstanding relatively high temperatures and of resisting longitudinal stretch. An exemplary length is 5½ inches. The tubular structures 18 are sized diametrically to provide an interior diameter to slidably receive and closely confine an associated movable wire section 22 therein. A preferred example of a material which can be utilized to form the wire receiving tubular structures 18 is polyimide having a wall thickness of 0.0005".

The wires 20 are preferably made of a kink resistant metal, preferably a shape memory metal such as nitinol. Preferably, the kink 26 is formed in memory as an acute included angle between the fixed and movable wire sections 24 and 22 which extend coextensively from the kink 26. A preferred range being 80° to 45° with 50° being a preferred angle. An exemplary dimension for the nitinol wires is within the range 0.006" to 0.0085".

Figure 7:
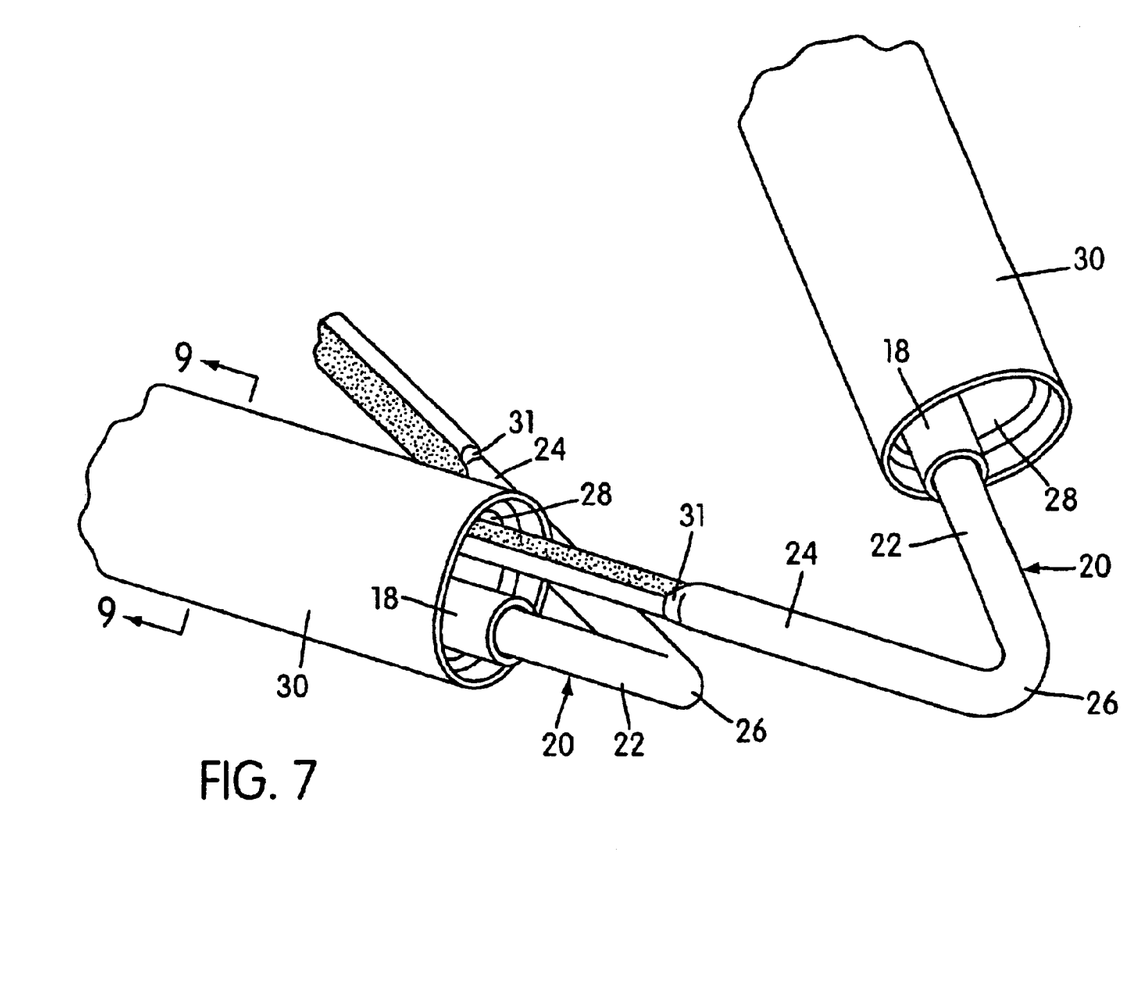
FIG. 7 is a perspective view illustrating an initial step in the assembly of the gripping and releasing mechanism according to the method of the present invention.
Figure 8:
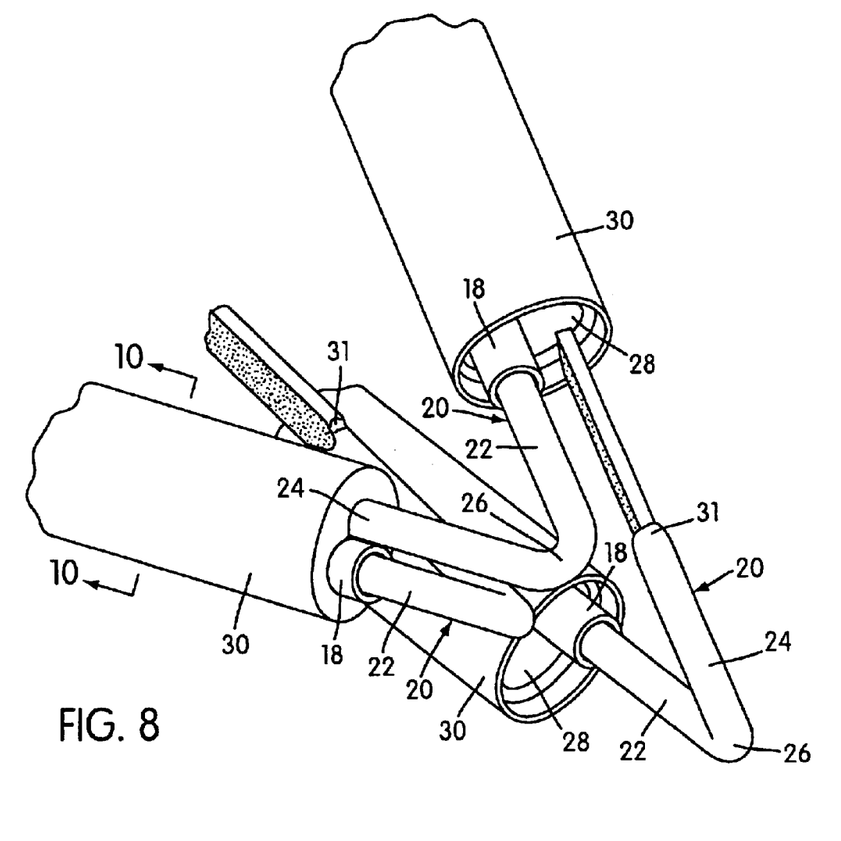
FIG. 8 is a view similar to FIG. 7 illustrating a subsequent step in the assembly.
Figure 9:
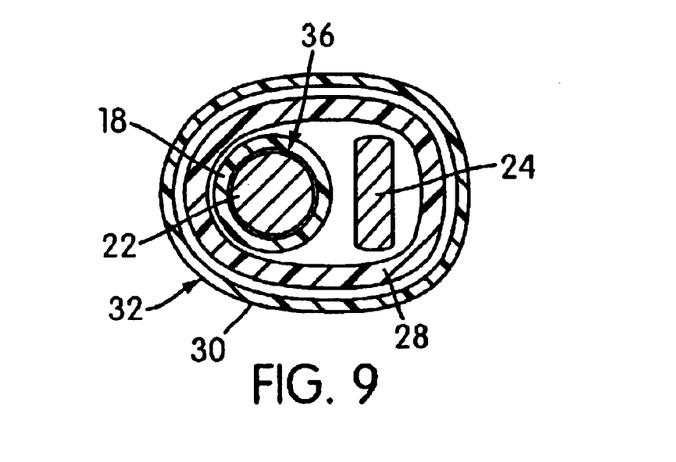
FIG. 9 is a sectional view taken along the line 9—9 of FIG. 7.

As best shown in FIGS. 7 and 8, preferably, the fixed wire section 24 of each wire 20 has a free end portion thereof flattened, as by a squeezing action between two rollers, so as to provide a pair of spaced shoulders 31 facing toward the associated kink 26. Preferably, the opposed exterior surfaces of each flattened portion are abraded, as indicated by the stippling in FIGS. 7 and 8 to enhance the adherence thereof to the thermoplastic material of the associated tubular element 28.

Figure 10:
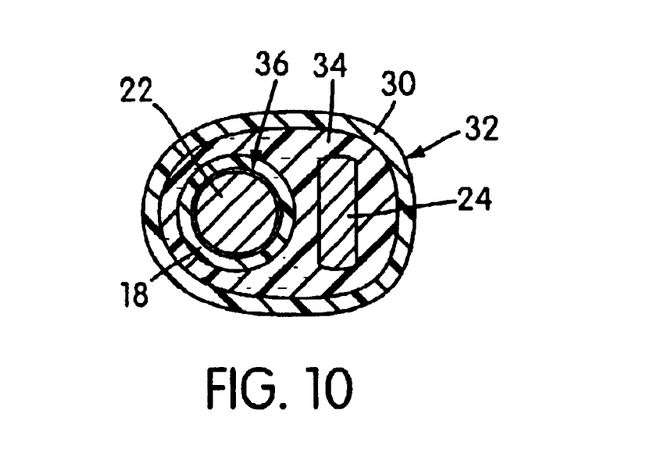
FIG. 10 is a sectional view taken along the line 10—10 of FIG. 8.

The tubular elements 28 are shown in FIGS. 7, 8 and 10. A preferred material is a 9% mixture of Ethylene Vinyl Acetate with low density polyethylene (LDPE/EVA). The interior diameter size of the surrounding tubular elements 28 are oversize with respect to exterior diameter size of the wire receiving tubular structures 18. An exemplary length for the tubular elements 28 is 2 cms which is slightly in excess of the length of the heat shrinkable sleeves 30, e.g. ¼ inch.

Each heat shrinkable sleeve 30 is preferably somewhat oversize in diameter with respect to the tubular elements 28 and is formed of a material having a relatively high shrink temperature. A preferred material is polyester resin (PET), although other suitable materials may be utilized.

Ultimately, the kinked wires 20, the distal end portions of the wire receiving tubular structures 18, the surrounding tubular elements 28, and the heat shrinkable sleeves 30 are assembled so as to form the gripping and releasing mechanism 14. In the assembly, a movable wire section 22 is disposed within each flexible tube 30 and a distal end portion of each flexible tubular structure 18 is assembled together with a fixed wire section 24, a tubular element 28, and a heat shrinkable sleeve 30 so that (1) the fixed wire section 24 extends along the exterior periphery of the flexible tubular structure 18 with the kink 26 disposed outwardly of the distal end thereof, (2) the tubular element 28 is disposed in surrounding relation to the fixed wire section 24 and the flexible tubular structure 18 and (3) the heat shrinkable sleeve 30 is disposed in surrounding relation to the tubular element 28 so that a short proximal end portion of the tubular element 28 extends beyond the proximal end of the heat shrinkable sleeve 30. It is noted that the surrounding position of the tubular element 28 with respect to the fixed wire section 24 insures that the shoulders 31 of the flattened free ends of the fixed wire sections 24 are covered by thermoplastic material.

Preferably, as shown in FIG. 8, each flexible tubular structure 18 is assembled with a fixed wire section 24, a tubular element 28 and a heat shrinkable sleeve 30 in the positions indicated, heat is applied progressively to the exterior of the heat shrinkable sleeve 30 of the assembly at a temperature and for a time sufficient to cause the heat shrinkable sleeve 30 to shrink or contract around the coextensive portion of the associated surrounding tubular element 28. The heat preferably is applied by a hot air blast at a temperature which will soften the thermoplastic material of the coextensive portion of the surrounding tubular element 28 causing it to flow into adhered contact with the exterior peripheries of the fixed wire section 24 and the distal end portion of the tubular structure 18. Once the heat is removed and the components are allowed to cool, the thermoplastic material of the coextensive portions of the surrounding tubular elements 28 serves to adhere each fixed wire section 24 to the exterior periphery of the distal end portion of the associated wire receiving tubular structure 18.

The sequential heating of each heat shrinkable sleeve 30 as it is assembled, as shown in FIGS. 7 and 8, is, as aforesaid, preferred because only one assembly need be maintained in position at one time and then fixed in that position by the application of heat. However, it is within the broadest aspects of the present invention to complete all three assemblies and then effect the heating.

Figures 5, 6A, 6B:
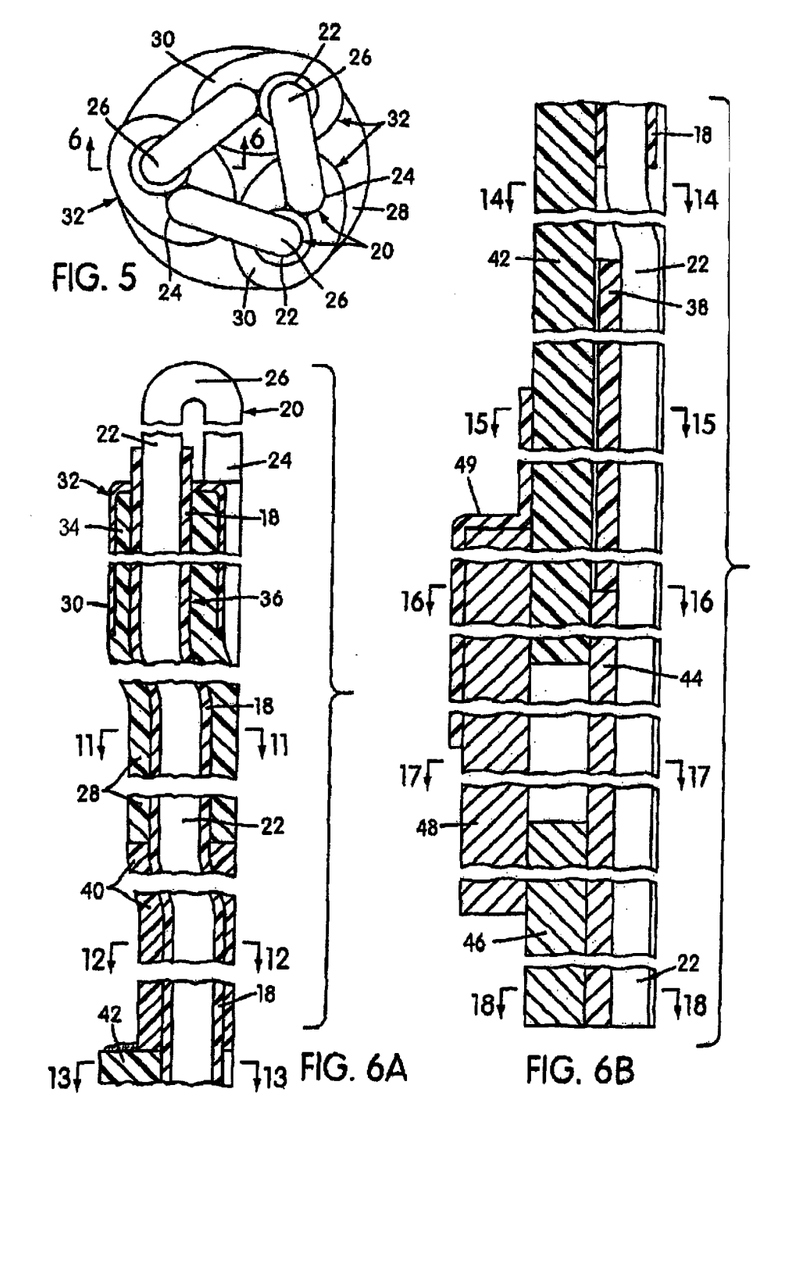
FIG. 5 is an enlarged top plan view of the gripping and releasing mechanism of the present invention showing the same in a closed position.
FIG. 6A is a fragmentary sectional view of a distal portion of the cannula assembly taken along the line 6—6 of FIG. 5.
FIG. 6B is a view similar to FIG. 6A of the remaining proximal portion of the cannula assembly.

In this way, there are formed at the distal end of the cannula assembly 12 three flexure elements 32, each of which, as shown in FIG. 6A, is comprised of the coextensive distal end portion of the associated wire receiving tubular structure 18, a fixed wire section 24, a surrounding body of molded thermoplastic material indicated at 34 in FIG. 6A and a coextensive surrounding short heat shrinkable sleeve 30 in a heat contracted condition defining the exterior molded shape of the body of thermoplastic material 34. The three flexure elements 32 are fixed together at their proximal ends in a manner hereinafter to be described so as to constitute fixed flexure elements 32 of the gripping and releasing mechanism 14. The distal portions of the movable wire sections 22 which move out of and are slidable within the fixed flexure elements 32 constitute movable flexure elements 36 of the gripping and releasing mechanism 14.

The fixing of the proximal ends of the fixed flexure elements 32 is preferably accomplished by using a heat shrinkable tube which is not shown in the drawings because it is used only as an assembly tool.

Figure 11:
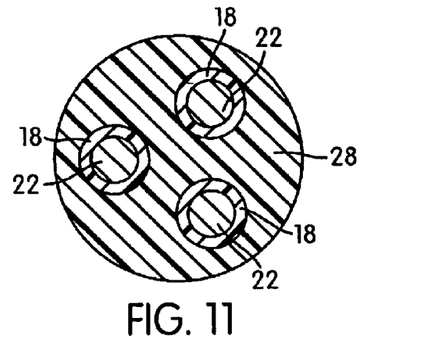
FIG. 11 is a cross-sectional view taken along the line 11—11 of FIG. 6A.

The heat shrinkable tube has an interior diameter sufficient to fit over the movable wire sections 22 extending from the tubular structures 18, the tubular structures 18 themselves, the short sections of the tubular elements 28 extending beyond the sleeves 30 and the sleeves 30 themselves. The length is sufficient to extend in slight overlapping relation to the proximal ends of the sleeves 30 and slightly beyond the proximal ends of the tubular elements 28. A preferred material for the heat shrinkable tube is fluorinated ethylene propylene (FEP). When so positioned, heat is applied to the exterior periphery of the heat shrinkable tube at a temperature and for a time sufficient to cause it to shrink and soften the material of the tubular elements 28 surrounded thereby causing the softened material to fuse together in surrounding adhered relation to the exterior surfaces of the tubular structures 18 as shown in FIG. 11. After cooling, the heat shrunk tube is razor cut and stripped off.

Figure 14:
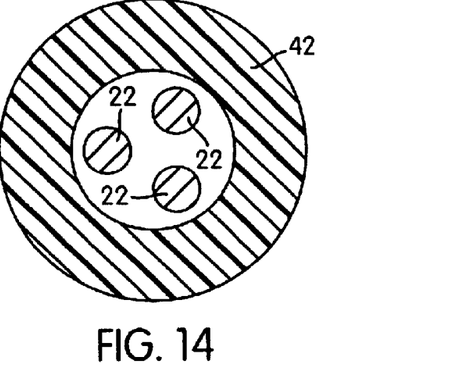
FIG. 14 is a cross-sectional view taken along the line 14—14 of FIG. 6B.

Preferably, the next step is to feed an elongated length of heat shrinkable tubing 38 over the three movable wire sections 22 extending from the proximal ends of the tubular structures 18. The length of the tubing 38 is somewhat less than the exposed extent of the movable wire sections 22. A preferred material for the tubing 38 is polytetrafluoroethylene (PTFE). The tubing 38 is extended over the wire sections 22 until the distal end is disposed in spaced relation to the proximal ends of the tubular structures 18 as shown in FIG. 14. This spacing is slightly more than the throw required to move the expandable and retractable gripping and releasing mechanism 14 between its movement limits.

Figure 15:
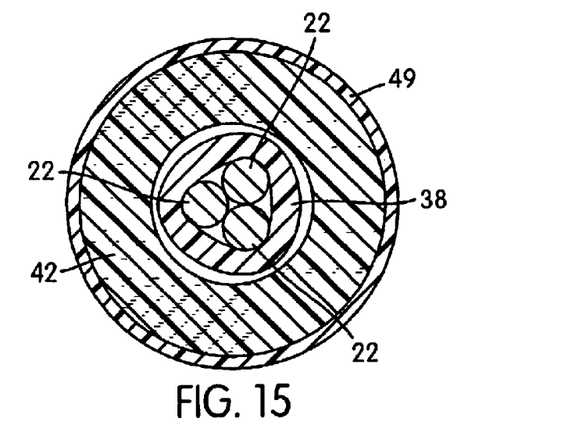
FIG. 15 is a cross-sectional view taken along the line 15—15 of FIG. 6B.
Figure 16:
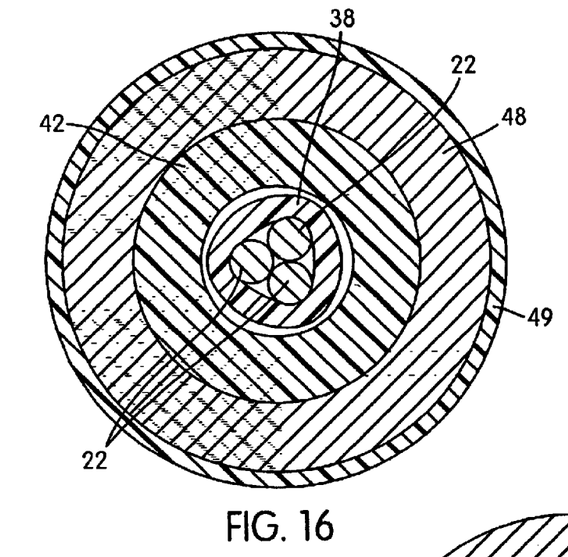
FIG. 16 is a cross-sectional view taken along the line 16—16 of FIG. 6B.

Here again, once positioned, heat is applied to the exterior surface of the tubing 38 at a temperature and for a time sufficient to shrink the tubing 38 into adhered relation to the exterior wire surfaces, as shown in FIG. 15. Preferably, the heat is applied longitudinally progressively along the length of the tubing 38 by a suitable known machine capable of performing such procedures.

Figure 12:
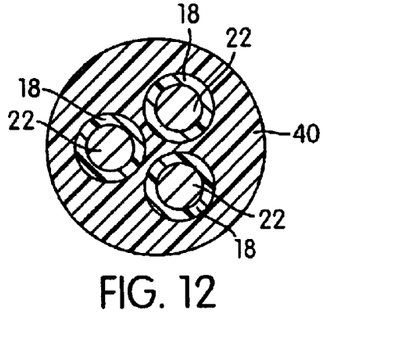
FIG. 12 is a cross-sectional view taken along the line 12—12 of FIG. 6A.
Figure 13:
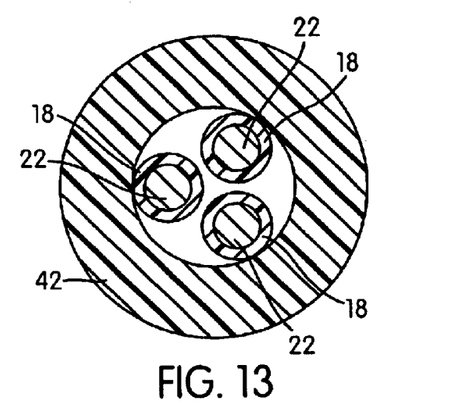
FIG. 13 is a cross-sectional view taken along the line 13—13 of FIG. 6A.

The preferred next step is to move a short tube 40 of thermoplastic material over the shrunk tubing 38, the adjacent bare wire section, and the proximal portions of the tubular structures 18 extending from the fused material of the tubular elements 28. The length of the tube is such that when its distal end is brought into abutting relation to the fused material of the tubular elements 28, the proximal end will not reach quite to the proximal ends of the tubular structures 18. A preferred material for the tube 40 is the same as that of the tubular elements 28. Here again, a heat shrinkable tube, similar to the one previously mentioned, is used as an assembly tool. The preferred material is FEP and the length is slightly longer than the tube 40 so that when disposed in position over the tube 40, a short distal end portion overlaps the fused material of the tubular elements 28 while short proximal end portions extend beyond the proximal end of the tube 40. As before, heat is applied to the exterior surface of the FEP tube at a temperature and for a time sufficient to shrink it and soften the material of the tube 40 into fused adhered contact with the exterior surfaces of the tubular structures surrounded thereby, as shown in FIG. 12. After cooling, the FEP tube is razor cut and stripped off. The covering and securing together of almost all of the few inches of extent of the tubular structures 18 beyond the tubular elements 28 provides a cannula section proximate to the gripping and releasing mechanism 14 at the distal end of the cannula assembly 12 which is particularly flexible and capable of being arcuately bent while allowing for controlled wire movement within.

The fixed part of the cannula assembly 12, in addition to this flexible section, also includes a main section formed by an elongated length of flexible tubing 42 which is preferably made of Polyethyl ethyl ketone (PEEK). The tubing 42 has an interior diameter slightly greater than the shrunk diameter of the PTFE tubing 38. Its length is such that its distal end can be extended into abutting relation to the proximal end of the fused material of the FEP tube 40 while its proximal end is spaced from the proximal ends of the wire sections 22. The distal end portion which also extends over the proximal end portions of the tubular structures 18 is glued in place by a suitable adhesive such as Lactite II. A UV curable adhesive, e.g. Dymax 204-CTH is preferably used in the butt joint between the distal end surface of the PEEK tubing 42 and the fused material of the FEP tube 40.

It is preferable to next prepare the proximal end section of the cannula assembly 12 thus far assembled for interconnection with the components of the moving assembly 16. The moving part of the cannula assembly 12, which includes the three wire sections 22 and the PTFE material of the tubing 38 adhered to the exterior periphery thereof, has an inner thin walled stainless steel hypo tube 44 suitably glued to the proximal end portion of the three wire sections 22. An example of a durable glued connection is to trim the PTFE material from the wire sections 22, roughen the exposed exterior surfaces of the wire sections 22, apply adhesive, such as Lactite M-31CL, to the roughened exterior surfaces and then slide the hypo tube 44 over the adhesive.

When the gripping and releasing mechanism 16 of the grasper 10 is in a closed position, the hypo tube 44 is positioned so that a short distal end portion is disposed within the proximal end position of the PEEK tubing 42. When in this position, an outer stainless steel hypo tube 46 glued over the inner hypo tube 44, for example, in the manner previously described, has its distal end spaced from the proximal end of the PEEK tubing 42 and its proximal end positioned to coincide with the proximal end of the inner hypo tube 44 and the proximal ends of the wire sections 22. The spacing of the distal end of the outer hypo tube 46 from the proximal end of the PEEK tubing 42 is slightly greater than the "throw" already mentioned.

The fixed part of the cannula assembly 12, which includes the previously described flexible section and the main section provided by the PEEK tubing 42, has a large diameter telescoping stainless steel hypo tube 48 suitably glued as before, exteriorly to a proximal end portion of the PEEK tubing 42.

Figure 17:
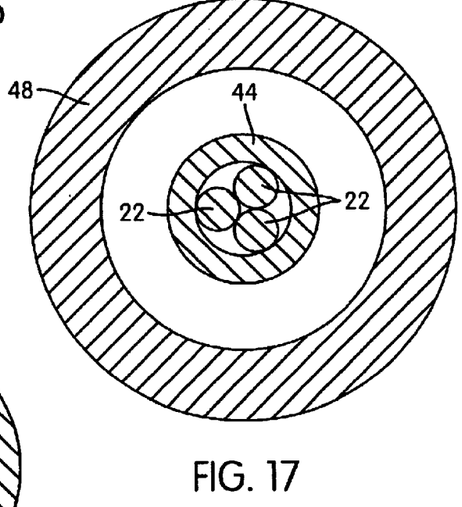
FIG. 17 is a cross-sectional view taken along the line 17—17 of FIG. 6B.
Figure 18:
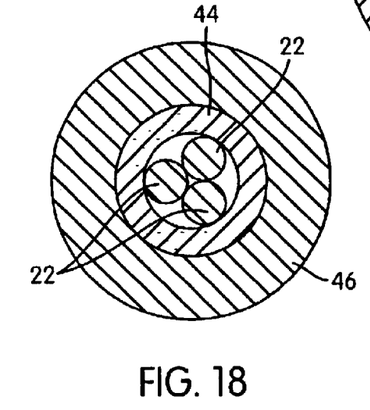
FIG. 18 is a cross-sectional view taken along the line 18—18 of FIG. 6B.

When the gripping and releasing mechanism 14 of the grasper 10 is in a closed position, a proximal end portion of the hypo tube 48 extends in telescoping relation over a distal end portion of the outer hypo tube 46, the proximal end of the telescoping hypo tube 48 being spaced a "throw" distance from the proximal end of the outer hypo tube 46, as shown in FIGS. 6B and 17.

The glued connection of the telescoping hypo tube 48 with the PEEK tubing 42 is enhanced by the provision of heat shrinkable tube 49 preferably made of polyolefin. The heat shrinkable tube 49 is heat shrunk so that a distal end portion thereof is adhered to a roughened exterior surface of the PEEK tubing 42 adjacent the telescoping hypo tube 48 and the remaining proximal end portion thereof is adhered to a roughened exterior surface of a distal end portion of the telescoping hypo tube 48.

Figure 2:
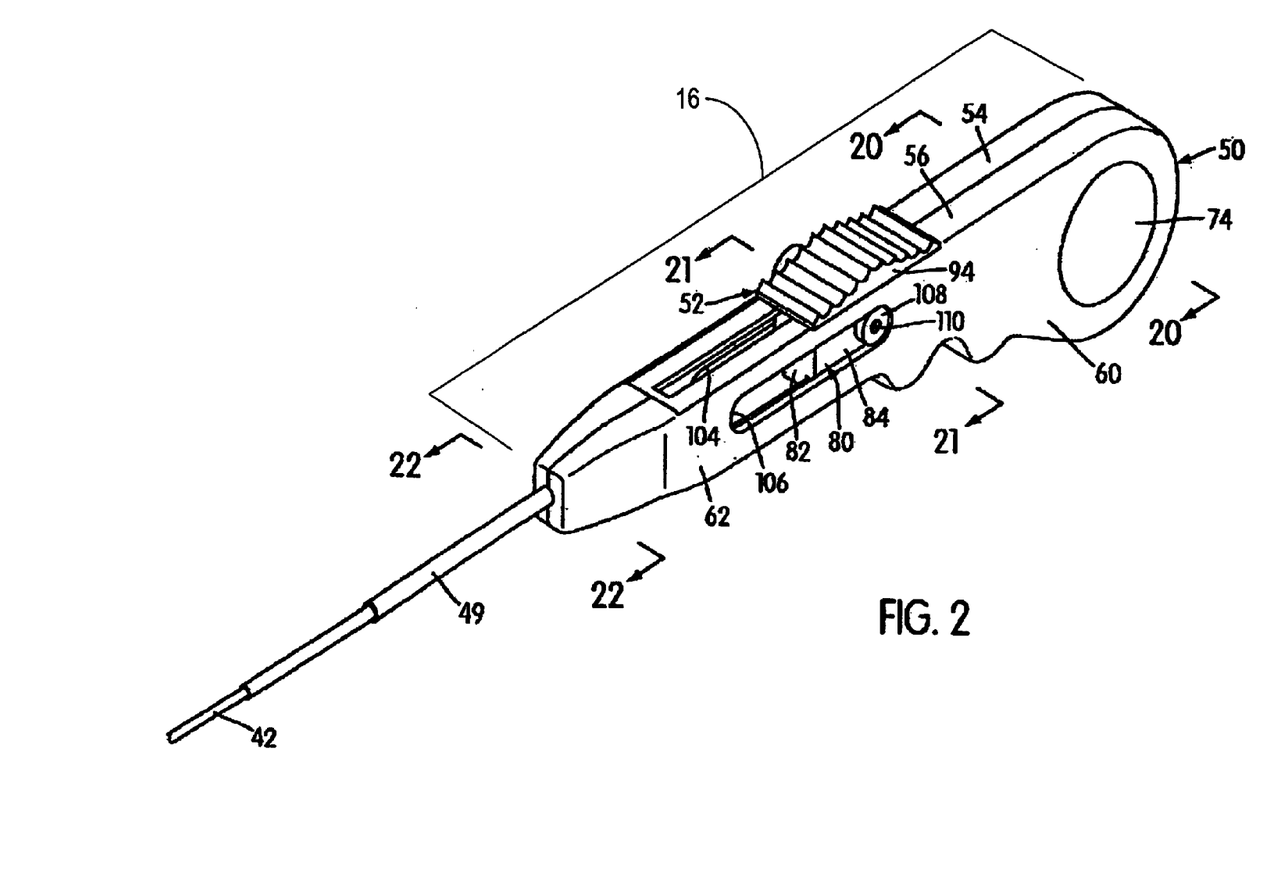
FIG. 2 is a fragmentary perspective view of a moving assembly and adjacent portion of the cannula assembly of the medical grasper showing the parts in a closed position corresponding to the position of the parts shown in FIG. 1.

The moving handpiece assembly 16 may assume any known configuration including the spring biased moving assembly disclosed in the aforesaid priority application. However, as shown, the handpiece assembly 16 is a known assembly manufactured and commercially sold by CR Bard, Inc. As best shown in FIG. 2, the moving handpiece assembly 16 includes a fixed housing assembly, generally indicated at 50, and a moving assembly, generally indicated at 52, slidably mounted in the fixed housing assembly 50 between limiting positions, one of which corresponds to the closed position of the gripping and releasing mechanism 14 and the other of which corresponds to the open position of the gripping and releasing mechanism 14.

Figure 19:
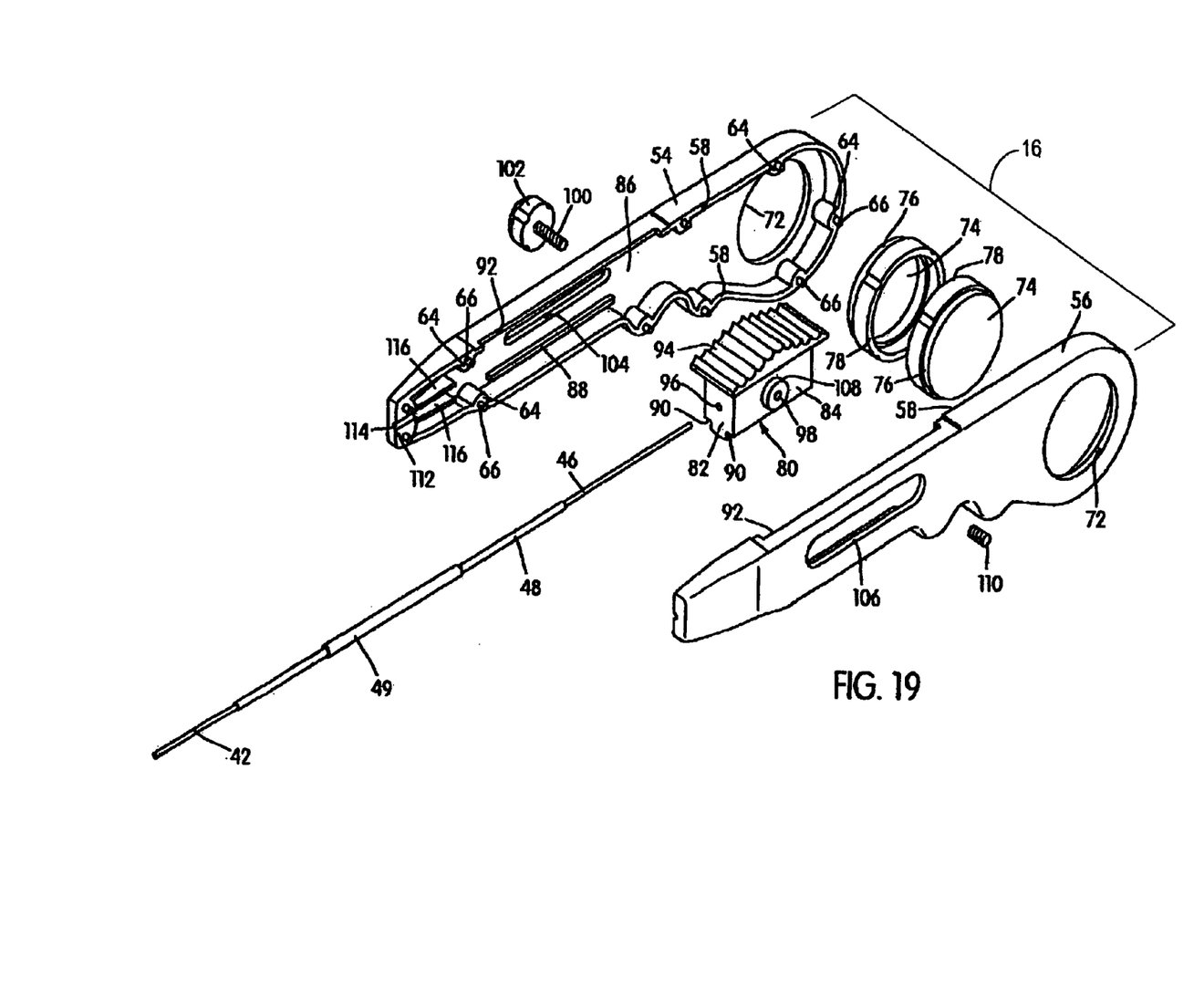
FIG. 19 is an exploded perspective view of the component parts of the moving handpiece assembly of the grasper.

The fixed housing assembly 50 includes two complementary split housing members 54 and 56, best shown in FIG. 19, molded of a suitable plastic material, such as ABS or polycarbonate. The housing members 54 and 56 are of shell-like construction, with edges 58 configured to be moved into complementary abutting relation with one another so as to form a three dimensional gun-like shape including a rear handle portion 60 configured to be gripped by one hand of a user and a barrel portion 62 extending forwardly therefrom from which the cannula assembly 12 extends.

Figure 20:
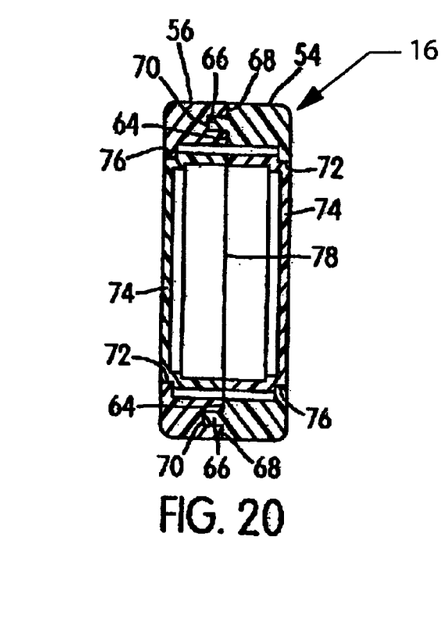
FIG. 20 is a cross-sectional view taken along the line 20—20 of FIG. 2.
Figure 21:
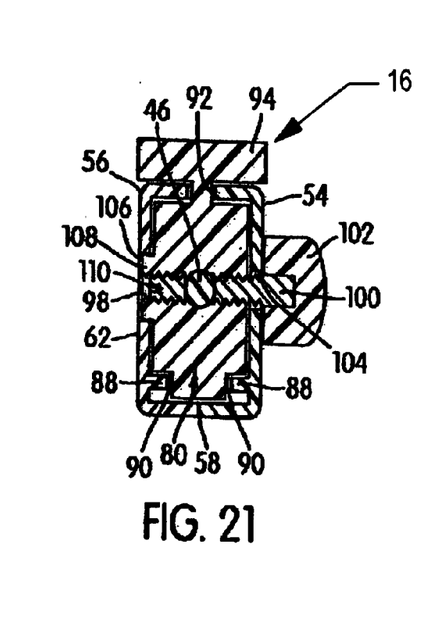
FIG. 21 is a sectional view taken along the line 21—21 of FIG. 2.

The housing member 54 includes a series of peripherally spaced bosses 64, each having a projection 66 extending from the central portion thereof. As best shown in FIG. 20, the housing member 56 includes a series of abutting bosses 68, each having a central opening 70 therein sized to receive a corresponding projection 66. The handle portions of the housing members 54 and 56 have large circular openings 72 therein each sized to receive therein a logo carrying circular member 74. The circular members 74 are of generally cup-like configuration each being peripherally recessed, as indicated at 76, to fit with an associated opening 72 and having circular edges 78 positioned to abut one another.

The moving assembly 52 includes a pusher member, generally indicated at 80, molded of a suitable plastic material, such as ABS or polycarbonate.

The pusher member 80 includes a rectangular body portion 82 having a width defined by planar exterior surfaces 84 configured to slidably engage complementary centrally located planar interior surfaces 86 provided by the housing members 54 and 56. Formed in the lower central portion of each housing member 54 and 56 below the associated planar surface 86 is a rail portion 88 positioned to be slidably engaged by a corresponding rail surface 90 formed along the associated lower corner of the body portion 82 below the associated planar surface 84.

Each housing member 54 and 56 has an elongated recess 92 formed in a central upper portion of the edge 58 thereof. The body portion 82 is suitably recessed along the upper extremities of the planar surfaces 84 to provide an upper section of reduced width which rides within the opening defined by the edges of the recesses 92.

The pusher member 80 also includes an upper thumb engaging portion 94 integral with the body portion 82 along the upper section thereof. The thumb engaging portion 94 extends transversely outwardly beyond the sides of the body portion to provide flange sections which overlie and can slide along the upper exterior surfaces of the housing members 54 and 56 adjacent the recesses 92. As best shown in FIGS. 2 and 19, the upper surface of the thumb engaging portion 94 is longitudinally convex and formed with spaced ridges to aid thumb manipulation.

The body portion 82 is formed with a longitudinally extending bore 96 sized to receive therein the outer hypo tube 46. The body portion 82 also is formed with a transversely extending threaded bore 98 which intersects at its central portion with a central portion of the bore 96.

The portion of the threaded bore 98 on the housing member 54 side of the longitudinal bore 96 is adapted to receive a threaded stem 100 of a knob 102. The housing member 54 has an elongated slot 104 formed in the central side wall thereof which enables the threaded stem 100 to be threaded into the threaded bore 98 and move with the pusher member 80 while the knob 102 is disposed exteriorly of the fixed housing assembly 50.

The opposite housing member 56 is formed with a comparable parallel slot 106 which has a width dimension larger than the width dimension of the slot 102. The larger width slot 106 is configured to receive therein a circular boss 108 formed integrally on the adjacent planar surface 84 of the pusher member 80. A set screw element 110 is adapted to be threadedly engaged in the portion of the threaded bore 98 adjacent the housing member 56.

The longitudinal bore 96 together with the threaded stem 100 and set screw element 110 provide the interconnection with the movable part of the cannula assembly 12. As previously indicated, the bore is sized to receive the outer hypo tube 46. After the hypo tube 46 is inserted in the bore, set screw element 110 can be used to lock the tube 46 in the bore 96.

Figure 22:
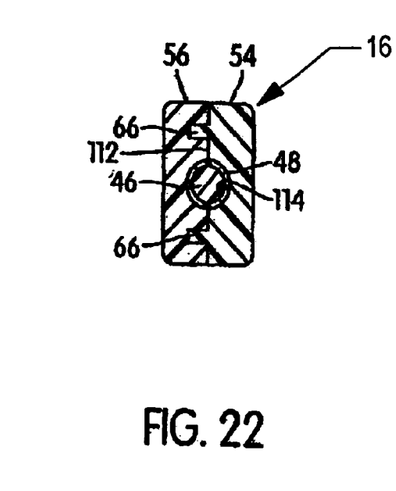
FIG. 22 is a sectional view taken along the line 22—22 of FIG. 2.

The interconnection with the fixed part of the cannula assembly 12 is provided by a large arcuate boss 112, best shown in FIGS. 19 and 22, formed in the forward end of each housing member 54 and 56 having a longitudinal groove 114 of half circle cross section therein. Also, as shown, in FIG. 19, there are two rearwardly extending reinforcing ribs 116 disposed just rearwardly of the arcuate boss 112.

The interconnection is accomplished in conjunction with the assembly of the housing members 54 and 56 together. This assembly, as well as the pre-assembly of the circular members 74 within the circular openings 72, is accomplished by applying an appropriate adhesive to the abutting surfaces of the parts and moving them together. Of course, the pusher member 80 with the attached cannula assembly 12 is properly positioned within the housing members 54 and 56 before they are moved together. During the movement together, the glued surfaces of the grooves 114 engage the exterior surface of the fixed telescoping hypo tube 48 adjacent the heat shrunk tube 49. Additional adhesive can be used between the ribs 116.

Operation

As previously indicated, the medical device 10 is made to cooperate with a scope. When used as a kidney stone grasper, typically, the scope will be entered into the kidney through the urinary canal. The medical device 10 with the gripping and releasing mechanism 14 and moving assembly 16 in the closed positions thereof, as shown in FIGS. 1 and 2, is fed through the central passageway of the scope. When the gripping and releasing mechanism 14 extends outwardly of the distal end of the passageway of the scope, the operator grasping the housing assembly 50 in one hand moves his thumb forwardly on the thumb engaging surface 94 of the digitally engageable pusher member 80. The pusher member 80 moves forwardly within the housing assembly 50 as the thumb pushes forwardly. Since the movable wire sections 22 are fixed within the inner and outer hypo tubes 44 and 46, they, in turn, are moved forwardly. Since the movable wire sections 22 are contained together in spaced relation to the normal ends of the tubular structures 18 by the PTFE material of the tubing 38, the individual movable wire sections 22 can now move individually within each containing tubular structure 18. The distal end portions of the movable wire sections 22, constituting the movable flexure elements 36 of the gripping and releasing mechanism 14, move outwardly of the distal ends of the wire receiving tubular structures 18. When the pusher member 50 has been moved from the closed limiting position thereof forwardly toward its opened limiting position through an operative opening stroke, as shown in FIG. 4, the gripping and releasing mechanism 14 will have been moved toward the open limiting position thereof into an expanded condition as defined by an annular series of transversely outwardly flexed fixed flexure elements 32 interconnected by an annular series of arcuately flexed portions of the movable flexure elements 36. The extent of the operative opening stroke is dependent upon the size of the stone to be extracted, but is normally limited by the engagement of the pusher member 80 with suitable stop surface provided by the housing assembly 54.

With the gripping and releasing mechanism 14 in its expanded condition, as shown in FIG. 3, the physician can then manipulate the open gripping and releasing mechanism 14 into surrounding relation to the stone within the kidney to be extracted. As soon as this stone surrounding relationship is established, the physician engages a thumb on the thumb engaging surface of the thumb engaging shape portion 94 of the pusher member 80 to pull the pusher member 80 rearwardly within the housing assembly 52. The rearward movement of the pusher member 80 is transmitted to the proximal end portions of the movable wire sections 22 which causes the movable flexure elements 36 of the gripping and releasing mechanism to move through a gripping stroke during which the movable flexure elements 36 are moved inwardly into the fixed flexure elements 32 to progressively retract the gripping and releasing mechanism 16 from its expanded condition into gripping relation to the stone, as shown in FIG. 5. The scope is then withdrawn from the patient's body with the gripped stone in the gripping and releasing mechanism 14 while holding the thumb pressure on the portion 94.

After withdrawal, the gripped stone can be released by simply digitally moving forwardly on the thumb engaging portion 94 to expand the gripping and releasing mechanism 14 and release the stone, after which the pusher member 80 can be returned to its closed limiting position.

It thus will be seen that the objects of this invention have been fully and effectively accomplished. It will be realized, however, that the foregoing preferred embodiments of the present invention have been shown and described for the purposes of illustrating the structural and functional principles of the present invention and are subject to change without departure from the spirit and scope of the appended claims.

What is claimed is:

1. A method of forming an annularly expanding and retracting gripping and releasing mechanism suitable for use as a stone extractor or medical where grasper comprises an annular array of fixed flexure elements fixed together at proximal ends thereof and corresponding movable flexure elements fixed with respect to distal ends of respective fixed flexure elements and movable within respective adjacent fixed flexure elements so that (1) movement of said movable flexure elements outwardly of said fixed flexure elements causes said fixed flexure elements to flex transversely outwardly and create an expanded condition defined by an annular series of transversely outwardly flexed fixed flexure elements interconnected by an annular series of arcuately flexed portions of said movable flexure elements; and (2) movement of said movable flexible elements when in an expanded condition in a direction inwardly of the fixed flexure elements causes the expanded condition to progressively retract, said method comprising:

providing (1) a series of flexible tubular structures; (2) a corresponding series of wires, each of which includes a movable wire section and relatively short fixed wire section integrally connected with one end of the movable wire section by a kink configured so that said wire sections extend in longitudinally coextensive relation therefrom; (3) a series of tubular elements of thermoplastic material; and (4) a series of heat shrinkable sleeves;

assembling a movable wire section within each flexible tubular structure and a distal end portion of each flexible tubular structure with a fixed wire section, a tubular element and a heat shrinkable sleeve so that (1) the fixed wire section extends along the exterior periphery of the flexible tubular structure with the kink disposed outwardly of the distal end thereof; (2) the tubular element is disposed in surrounding relation to the fixed wire section and the flexible tubular structure; and (3) the heat shrinkable sleeve is disposed in surrounding relation to the tubular element, and applying heat to the exterior of each heat shrinkable sleeve at a temperature sufficient to contract the sleeve and soften the thermoplastic material of the tubular element surrounded thereby so that the contraction of the sleeve molds the softened thermoplastic material into adhered contact with the exterior surfaces of the surrounded fixed wire section and flexible tubular structure, and fixedly securing said flexible tubular structures together adjacent the proximal ends of the heat shrinkable sleeves disposed in surrounding relation to said tubular elements.

2. A method as defined in claim 1, wherein heat is applied to each heat shrinkable sleeve as aforesaid in sequence as each heat shrinkable sleeve is assembled as aforesaid.

3. A method as defined in claim 2, wherein prior to the assembly of each fixed wire section, each fixed wire section is rolled so as to be flattened and create opposed inwardly facing shoulders thereon, and during assembly, the shoulders of each fixed wire section are surrounded by an associated tubular element.

4. A method as defined in claim 3, wherein an exterior surface of each flattened fixed wire section is abraded to enhance its adherence to said thermoplastic material.

5. A method as defined in claim 1, wherein said wires are formed of nitinol, said tubular structures are tubes formed of polyimid, the thermoplastic material of said tubular elements is a mixture of low density polyethylene and ethel vinyl acetate and said heat shrinkable sleeves are formed of polyester resin.

6. A method as defined in claim 1, wherein each tubular element includes a proximal end portion extending beyond a proximal end of the surrounding heat shrinkable sleeve and the step of fixedly securing said flexible tubular structures comprises surrounding the proximal end portions of said tubular elements with a heat shrinkable tube, heating the heat shrinkable tube sufficiently to shrink it and mold the softened thermoplastic material of the surrounded tubular element proximal end portions into adhered relation to adjacent exterior surfaces of said flexible tubular structures and then removing said heat shrinkable tube.

7. A method as defined in claim 6, wherein said tubular structures include proximal ends disposed a relatively short distance from the position of fixed securement thereof as compared with the distance said movable wire sections extend from the proximal ends of said tubular structures and said method includes the further step of heat shrinking a length of heat shrinkable tubing around the extending movable wire sections from a position at the proximal end of a cannula assembly to a position spaced from the proximal ends of said tubular structures defining a throw distance for said gripping and releasing mechanism.

8. A method as defined in claim 7, wherein said heat shrinkable tubing is made of polytetrafluoroethylene.

9. A method as defined in claim 8, wherein said heat shrinkable tubing is heated progressively along its length.

10. A method as defined in claim 9, including the step of adhering said tubular structures together from the position of securement to a position adjacent and spaced from the proximal ends thereof.

11. A method as defined in claim 10, wherein said adhering step comprises surrounding the aforesaid extent of said tubular structures with a tube of thermoplastic material, surrounding the tube of thermoplastic material with a heat shrinkable tube, heating the heat shrinkable tube to shrink it and cause the thermoplastic material of said tube of thermoplastic tube to soften and be molded in adhered relation to the exterior surfaces of the tubular structures and then removing the shrunken heat shrinkable tube.

12. A method as defined in claim 11, wherein said tube of thermoplastic material is made of a mixture of low density polyethylene and ethyl vinyl acetate.

13. A method as defined in claim 12, wherein said heat shrinkable tube is made of polyolefin.

14. A method as defined in claim 11, including the step of adhering a length of tubing in surrounding relation to the exposed proximal ends of said tubular structures.

15. A method as defined in claim 14, wherein said length of tubing is made of polyethyl ethyl ketone.

* * * * *

UNITED STATES PATENT AND TRADEMARK OFFICE
CERTIFICATE OF CORRECTION

| | | |
|---|---|---|
| PATENT NO. | : 7,210,210 B2 | Page 1 of 1 |
| APPLICATION NO. | : 10/445086 | |
| DATED | : May 1, 2007 | |
| INVENTOR(S) | : Lippitt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this
Sixth Day of February, 2024

Katherine Kelly Vidal
*Director of the United States Patent and Trademark Office*